United States Patent [19]
Glaunsinger et al.

[11] Patent Number: 5,635,136
[45] Date of Patent: Jun. 3, 1997

[54] APPARATUS FOR SENSING COMBUSTIBLE GASES EMPLOYING AN OXYGEN-ACTIVATED SENSING ELEMENT

[75] Inventors: William Glaunsinger, Chandler; Ian Sorensen, Phoenix, both of Ariz.; Mahesan Chelvayohan, El Torro, Calif.

[73] Assignee: Arizona Board of Regents, Tempe, Ariz.

[21] Appl. No.: 456,649

[22] Filed: Jun. 2, 1995

Related U.S. Application Data

[62] Division of Ser. No. 311,101, Sep. 23, 1994, Pat. No. 5,521,099.

[51] Int. Cl.$^6$ .................................................. G01N 30/95
[52] U.S. Cl. ........................ 422/88; 422/90; 422/98; 422/94; 436/151; 436/137; 73/23.31; 73/31.05
[58] Field of Search .......................... 436/149, 151, 436/158, 152, 136, 137; 422/83, 88, 90, 94, 98; 73/23.31, 31.05, 31.06

[56] References Cited

U.S. PATENT DOCUMENTS

| | | | |
|---|---|---|---|
| 3,989,463 | 11/1976 | Klein et al. | 361/280 |
| 4,686,847 | 8/1987 | Besocke | 73/24.01 |
| 4,724,008 | 2/1988 | Bell et al. | 134/2 |
| 4,828,673 | 5/1989 | Maeda | 204/427 |
| 4,883,959 | 11/1989 | Hosoki et al. | 250/306 |
| 4,953,387 | 9/1990 | Johnson et al. | 73/25.03 |
| 5,386,715 | 2/1995 | Evans et al. | 73/31.05 |

Primary Examiner—James C. Housel
Assistant Examiner—Rachel Heather Freed
Attorney, Agent, or Firm—Meschkow & Gresham, P.L.C.

[57] ABSTRACT

A combustible gas sensor having a noble metal sensor element with a surface that is heated above a critical temperature at which the surface is able to dissociate oxygen in a gas stream and adsorb the oxygen onto its surface. The adsorbed oxygen present on the noble metal surface enhances the reactivity of the sensor element and permits it to react with combustible gases that otherwise would have little or no affinity for the sensor element. The balance of adsorbed oxygen and combustible gas species on the sensor surface cause a change in an electrical property that is used to determine the presence or identity of a combustible gas, or to derive a concentration measurement. The electrical property measured to determine the presence, identity, or concentration of combustible gas includes the work function of the noble metal surface, which may be measured by incorporating the sensor element as a component of a variable capacitor contained in an electrical circuit adapted to measure change in current caused by the change in capacitance of the variable capacitor.

14 Claims, 5 Drawing Sheets

APPARATUS FOR SENSING COMBUSTIBLE GASES EMPLOYING AN OXYGEN-ACTIVATED SENSING ELEMENT

This is a divisional of application Ser. No. 08/311,101 filed on Sep. 23, 1994, now U.S. Pat. No. 5,521,099.

BACKGROUND OF THE INVENTION

The present invention relates to the detection and concentration measurement of combustible gases including, for example, the detection and measurement of concentrations of combustible gases in ambient air and, more particularly, to a combustible-gas sensing method employing a gas sensing apparatus having a relatively pure noble metal or noble metal alloy sensing element that, when maintained at a predetermined elevated temperature, exhibits the ability to react with combustible gases that otherwise would have little or no affinity for the sensing element.

Current sensor methods for monitoring and controlling combustible gases and their by-products employ sensors that suffer from at least one of the following drawbacks: poor long-term stability; need for frequent maintenance and calibration; low sensitivity to the gas being monitored; and high sensitivity to common interference gases including water vapor, with the latter being perhaps the most serious deficiency for many environmental applications.

For example, semiconductor gas sensors are normally plagued by high sensitivity to interference gases present in ambient air, such as common solvents and water vapor. Especially serious is the interference caused by water vapor, which is present in virtually all ambient air and which has a similar effect on semiconductor sensors as the target combustible gases such devices are intended to detect. U.S. Pat. No. 4,911,892 to Grace et al. (the '892 patent) discloses a semiconductor gas detection apparatus having enhanced capability for rejecting interference gases. Although improvements to semiconductor sensors such as those disclosed in the '892 patent may help to limit error, the semiconductor gas sensor's inherent sensitivity to common interference gases remains.

U.S. Pat. No. 3,714,562 to McNerney and U.S. Pat. No. 5,010,021 to Bell et al. disclose a gas detection method using a sensor comprising a relatively pure thin noble metal film sensor element selected for its chemical affinity for the target gas to be detected (hereinafter "metal affinity" gas sensors). When a sample mixture containing the target gas is passed over the sensor, the target gas adsorbs onto the surface of the sensor element causing the sheet resistance of the element to change. This resistive change is measured and, by comparison to a data base, converted into concentration units.

Metal affinity gas sensors do not exhibit the same sensitivity to water vapor as do semiconductor gas sensors. They are, however, limited to detecting target gases that have a natural affinity for the sensor surface at ambient temperature and they cannot be used by themselves to sense dynamic changes in concentration of the target gas because the sensor element surface reacts with the target gas to form stable surface species. These stable species saturate the sensor surface and, once its surface is saturated, the sensor cannot be used until it is regenerated, for example, by heating to desorb the compounds, or by rinsing with ozone.

Combustible gases, such as most hydrocarbons, which are able to react readily with oxygen, are critical to human existence. Because they represent a major source of energy as well as raw materials, these substances are essential to many industrial activities. However, their widespread use generates various hazards ranging from pollution to toxicity and even fire and explosion. Combustion is a major source of air pollution, much of which could be reduced by timely sensing of combustion products to indicate an out-of-specification combustion condition, and, of course, explosion caused by undetected leakage of combustible gases is an all-too-common occurrence. Unfortunately, shortcomings inherent in current gas sensor methods and devices have prevented widespread use of sensors capable of continuous operation to monitor combustible gases to avoid these and other similar occurrences.

For the foregoing reasons, there is a critical need for a combustible gas sensor that can be used continuously to detect and determine the concentration of a wide variety of combustible gases in the atmosphere or in a gas stream without being subject to false alarms caused by water vapor or other interference gases, yet having high sensitivity, fast dynamic response to changes in concentration, and the ability to distinguish between a variety of combustible gases.

SUMMARY OF INVENTION

The present invention is a method and apparatus that satisfies the need for a gas sensor that meets the foregoing requirements. The invention takes advantage of the fact that certain noble metals are able to become "oxygen activated" when maintained above a certain threshold temperature (the "oxygen activation temperature") and exposed to a gaseous mixture containing oxygen. By "oxygen activated" it is meant that these metals are able to dissociate oxygen gas in the mixture and adsorb the resulting atomic oxygen onto their surfaces without forming stable oxides; and once oxygen activated, they are able to react with combustible gases that otherwise would have little or no affinity for these metals. These metals will remain oxygen activated in the presence of oxygen over a range of temperatures above the oxygen-activation temperature up to a second threshold temperature (the "oxygen dissociation temperature") above which surface oxygen atoms recombine into oxygen gas and are desorbed from the surface. Above the dissociation temperature, the metals exhibit little or no enhanced reactivity with combustible gases. At various temperatures between the oxygen activation temperature and the oxygen dissociation temperature, oxygen-activated metals exhibit varying degrees of enhanced reactivity caused by the effect of temperature on the ability of the target gas species to adsorb on the metal surface before reacting with the surface oxygen.

According to the present invention, a target combustible gas is detected and its concentration measured by exposing a gaseous mixture containing oxygen to a noble metal sensor element maintained at a preselected temperature between the metal's oxygen activation temperature and its oxygen dissociation temperature. A baseline measurement of an electrical property of the sensor element, such as its work function, is taken after the surface has become oxygen activated. As a target combustible gas is introduced into the mixture, or as the sensor is introduced into a mixture already containing a combustible gas, the work function of the sensor element changes as the combustible gas reacts with the oxygen-activated surface of the sensor element. The work-function change is directly related to the concentration of the combustible gas within the mixture and is used to derive a concentration measurement.

The surface reactions of the sensor element are dynamic, that is, the reactions are ongoing with the sensor surface being continuously replenished with oxygen from the gaseous mixture. Therefore, the work function of the sensor element responds almost instantaneously to any changes in the concentration of the combustible gas within the mixture. When used in this manner, a single sensor element is able to determine the instantaneous concentration of a single known combustible gas or to detect the presence of a plurality of combustible gases individually or in combination.

Of particular interest, however, are that the work function response of a given sensor element as a function of temperature varies uniquely depending on the species of combustible gas within the mixture and that different sensor element materials exhibit different responses to the same combustible gas. Accordingly, in addition to being capable of measuring concentration of a known combustible gas, a single sensor element is capable of distinguishing between various combustible gases based on their work-function "signatures." An array of sensor elements of different materials at different temperatures would be capable of determining the identity and concentration of a plurality of combustible gases within the same mixture.

An object of the present invention, then, is to utilize the oxygen activation phenomenon as the basis for a gas sensor having improved sensitivity for target gases with decreased sensitivity to interference gases.

Another object is to provide a highly sensitive combustible gas sensor capable of continuous operation under ambient conditions and having wide detection capability.

A further object is to provide a noble metal gas sensor capable of determining the identity and concentration of various target gases.

BRIEF DESCRIPTION OF THE DRAWINGS

Still other objects and advantages of the present invention will become readily apparent to those skilled in this art from a consideration of the following detailed description of the presently-contemplated best mode of practicing the invention, by reference to a preferred embodiment of the invention disclosed in conjunction with the accompanying figures of drawing, in which.

DETAILED DESCRIPTION OF THE PREFERRED EMBODIMENT

When a noble metal is oxygen activated, the surface-adsorbed oxygen reacts readily with combustible gases, where present, to form quasi-stable surface intermediate products. These intermediate products then react to form stable oxidation products that are driven off the surface and replaced by more atomic oxygen. Oxygen activation occurs only with noble metals. Transition metals, such as cobalt, nickel and copper form stable oxides and so cannot be used as oxygen-activated sensor elements.

Referring to FIG. 1, it is believed that the surface reactions proceed according to a generalized acid-base reaction. FIG. 1(a) contains a representation of a noble metal surface 10 having molecules 11 at the surface. The metal surface 10 is shown at a temperature below its oxygen-activation temperature, exposed to a gaseous mixture 12 that contains oxygen. Below its oxygen-activation temperature ($T_o$), the exposed metal surface 10 neither dissociates oxygen from the gaseous mixture nor exhibits a tendency to react readily with the target combustible gas. FIG. 1(b) illustrates the oxygen activation of the metal surface 10 at a temperature above $T_o$, at which the surface causes the dissociation of oxygen gas ($O_2$) and adsorbs the atomic oxygen (O) onto its surface.

Figure 1A:
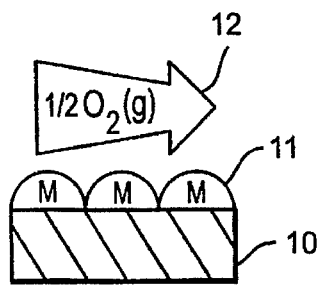
FIG. 1(a)–(e) illustrates one theoretical stepwise mechanism for the oxygen-activation process exploited by the present invention.
Figure 1B:
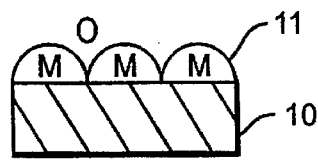
Figure 1C:
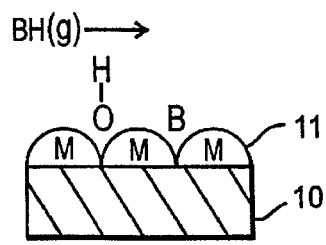

In FIG. 1(c), the target gas BH, contained in gaseous mixture 12, is adsorbed and dissociated on the metal surface 10. This surface reaction proceeds according to the general acid-base reaction $BH(g) + O_a \rightarrow B_a + (OH)_a$, where B is the residual resulting from the dissociation of a BH molecule and OH is the hydroxyl species resulting from the partial oxidation of hydrogen from the BH molecule. The subscript "a" refers to the status of the chemical species as being adsorbed on the surface.

Figure 1D:
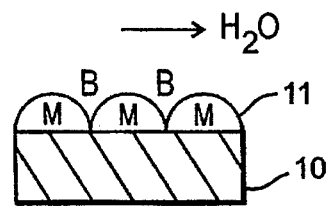
Figure 1E:
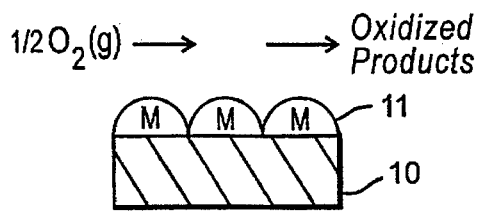

FIG. 1(d) is a representation of the adsorption and dissociation of a second molecule of BH on the metal surface 10. Finally, referring to FIG. 1(e), the metal surface 10 is shown as regenerated for another cycle of operation by the oxidation of the residual B on the metal surface by $O_2$ in the gaseous mixture.

Since only the metal surface participates in the oxygen-activation process, the metal can be in the form of a thin film, thick film, foil, or plate. The thin-film form is preferred, however, because it is economical where precious metals are involved, permits greater design flexibility, and allows close conformity to differing surface contours.

Figure 2:
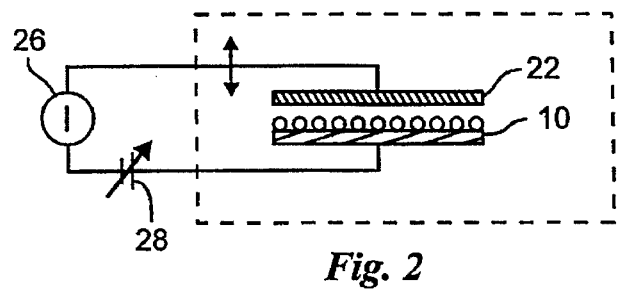
FIG. 2 is a schematic drawing of an electrical circuit for utilizing the combustible-gas sensor element in FIG. 1.

The presence of atomic oxygen and other adsorbed products on the surface has an effect on the electrical properties of the noble metal surface itself. FIG. 2 is a schematic drawing of an electrical circuit 20 for detecting the change of one such property, the work function of surface 10. The circuit 20 includes a variable direct current (D.C.) voltage source 28, a means for detecting alternating current (A.C.), such as an ammeter 26, a stationary sensor surface 10 composed of gold, platinum or other noble metal or noble metal alloy that exhibits the capability of oxygen activation as described with reference to FIG. 1 above and a reference surface 22. Reference surface 22, composed of a material that is incapable of becoming oxygen-activated, for example chromium-contaminated gold or gold at a temperature below its oxygen activation temperature, is juxtaposed in a spaced-apart, confronting relationship to surface 10, and is adapted to be movable toward and away from the confronting surface 10, as further described with reference to FIG. 5 below, to create a parallel-plate capacitor in which the gap between the plates can be varied in a periodic fashion. Oscillation of the reference plate is preferred because the reference surface, in contrast to the sensor surface, is not heated. This arrangement allows both the heat loss from the sensor plate and the mass of the reference plate to be minimized. The sensor surface 10 and reference surface 22 function as a parallel-plate capacitor, with the gap between them allowing introduction of a gaseous mixture containing the combustible gas to be detected.

The charge on the capacitor plates is related to the capacitance, C, and the voltage across the capacitor, V, by the equation $$Q = CV$$

Varying the gap between the plates in a fluctuating manner causes a fluctuating change in both the plate charge and capacitance resulting in a fluctuating current flow through the circuit 20 that is described by taking the derivative with respect to time of the above equation:

$$\frac{dQ}{dt} = \frac{dC}{dt} V$$

The voltage V is comprised of $V_b$, the bias voltage and $\Delta\phi$, the difference in work function between the plates. Since the current, i, is the time derivative of the charge Q (i.e., dQ/dt), the above equation becomes:

$$i = \frac{dC}{dt} (V_b - \Delta\phi) \qquad (2)$$

The work-function difference between the plates can be measured by adjusting the D.C. bias voltage from source 28 to reduce the alternating current measured by ammeter 26 to zero. In practice, instead of using an ammeter, both higher sensitivity and convenience of operation can be achieved by detecting and amplifying the alternating voltage associated with the alternating current by conventional means using, for example, a lock-in amplifier. The voltage output of the lock-in amplifier may also be fed into an automatic controller that is part of a feedback circuit loop to provide the appropriate bias voltage to maintain at all times a zero-current condition.

If the substrate of reference surface 22 is a magnetizable material, it can be made to vibrate by an alternating magnetic field produced by an electromagnetic coil driven by a frequency generator. It should be understood, however, that any means of inducing a variable capacitance between sensor surface 10 and reference surface 22 will accomplish the same result. It may also be possible to induce a periodic mechanical oscillation of reference surface 22 using piezoelectric means. Alternately, it may be possible to induce a variable capacitance by periodically altering the dielectric constant between the two surfaces, for example, by means of a variable dielectric material, or by using, as a reference, a semiconductor device such as a metal-insulator-semiconductor (MIS) structure, in which the dimension of the depletion layer can be modulated. Likewise, any capacitor configuration that permits gas flow between the sensor and reference element will also accomplish the same result. For example, the sensor and reference plates may be arranged concentrically.

Figure 3:
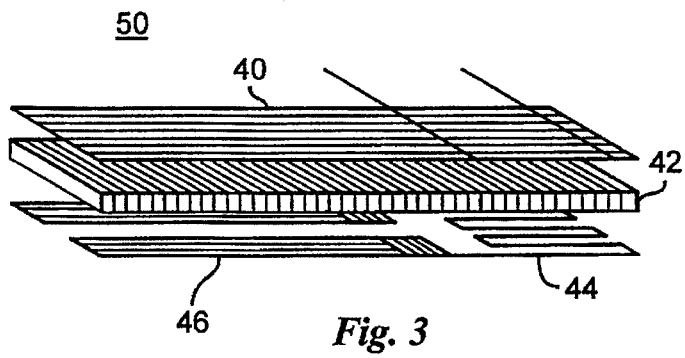
FIG. 3 is a perspective view of an illustrative embodiment of a sensor element used in the present invention.

FIG. 3 is a perspective view of an illustrative embodiment of the gas sensor element assembly 50 of the present invention. Substrate 42 is composed of alumina 2.5 cm long by 0.6 cm wide by 0.064 cm thick having a surface roughness of approximately 2 microns. The planar dimensions are unimportant; however, for good heat transfer, the thickness of the substrate should be kept to the minimum necessary for the structural integrity of the assembly. A thick-film resistive heater 44 is applied to one surface of the substrate by depositing resistive nickel in a serpentine pattern, having thick film silver electrodes 46. In an alternative embodiment, heater overglaze is applied by conventional means to the resistive heater 44 to permit sustained operation at temperatures of up to 500° C. It should be understood that the means for heating the sensor element is immaterial provided the appropriate temperature can be maintained. It would be equally acceptable to heat the gas stream itself to maintain the sensor element at the appropriate temperature. On the side of the substrate opposite the heater element, a thin-film noble-metal sensor element 40 is vapor deposited. The exposed surface of sensor element 40 comprises sensor surface 10, as described with reference to FIG. 2. For improved adhesion, a very thin film of chromium (less than about 50Å) can be deposited first, followed by a relatively thick (greater than about 1,000Å) film of noble metal. Typical thicknesses for the sensor elements are 500–6,000Å. Since the gas sensing occurs on the surface of the sensor element, however, the actual thickness is immaterial, as long as the noble metal film forms a continuous deposit on the substrate. Accordingly, sensor elements may be in the form of thin film, thick film, foil, or plate. Both gold and platinum sensor elements 40 have been made successfully by ordinary vapor deposition techniques.

Figure 4:
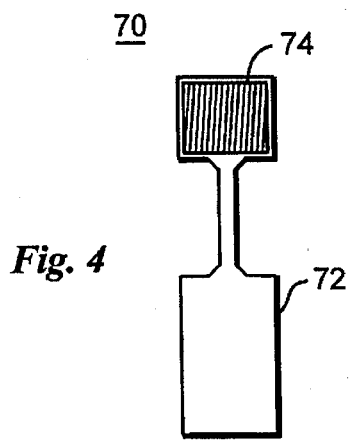
FIG. 4 is a plan view of an illustrative embodiment of a reference element used in the present invention.

FIG. 4 is a plan view of an illustrative embodiment of reference element assembly 70 of the present invention. Substrate 72 is composed of conventional spring steel. Reference body 74 is composed of a layer of chromium deposited on substrate 72 followed by a layer of gold. The surface of reference body 74 comprises reference surface 22 as described with reference to FIG. 2. The presence of the chromium layer underneath the gold allows chromium to diffuse through the gold film upon heating to temperatures up to 300° C., thereby contaminating the gold surface and disabling its ability to become oxygen activated. The chromium layer needs to be sufficiently thick to provide a stable reference surface for extended operation of the capacitor at elevated temperatures. Chromium films thicker than approximately 1,000Å provided a stable reference surface for several weeks at temperatures up to 500° C. Reference surfaces may also be prepared in several other ways, including by (i) depositing a relatively thick overlayer of chromium (greater than about 1,000Å) on gold followed by thermal annealing at temperatures up to 300° C.; (ii) depositing only a thick film of chromium; or (iii) using the bare surface of a stainless steel plate. Because only the exposed surface of the reference element must be incapable of becoming oxygen activated, the total thickness of the reference element is immaterial. Accordingly, reference elements may be fabricated in the form of thin film, thick film, foil, or plate. Chromiated reference surfaces can also be refurbished by further deposition of a relatively thick layer of chromium.

Figure 5A:
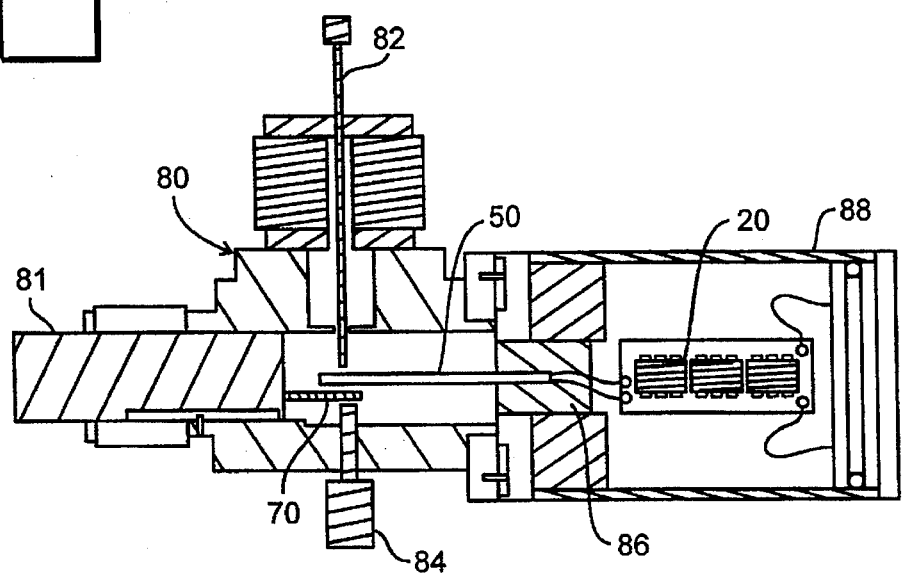
FIG. 5(a)–(b) are cross sectional views of an illustrative embodiment of an apparatus embodying the present invention.
Figure 5B:
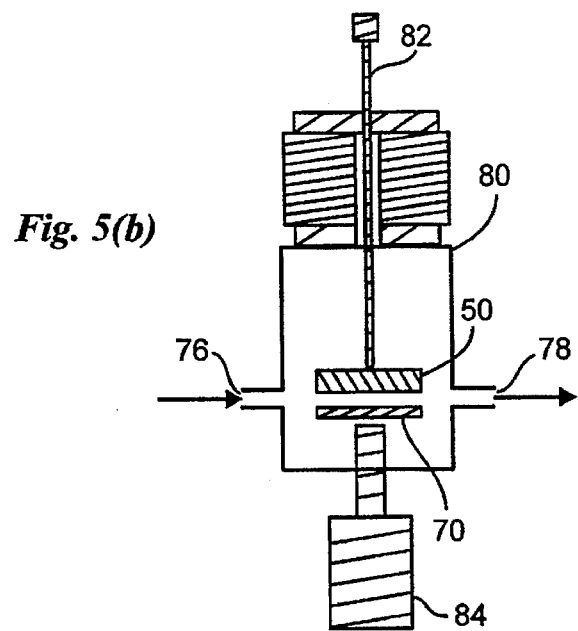

FIGS. 5(a) and 5(b) are cross-sectional views of an illustrative embodiment of the invention. Referring to FIG. 5(a), sensor element assembly 50 is supported by structure 80. Temperature probe 82 is a conventional thermocouple probe supported by structure 80 such that the thermocouple element of the probe is in contact with or in close proximity to sensor element 50. In lieu of a temperature probe, the power inputted to the heating element may also be used to derive a temperature. Reference element assembly 70 is supported at one end by arm 81 inserted into structure 80, reference element 70 forming a cantilever juxtaposed in a spaced apart confronting configuration parallel to element assembly 50. Reference element assembly 70 is caused to oscillate mechanically by subjecting it to an oscillating magnetic field produced by the extended metal core of an electromagnetic coil 84. In practice, an average separation between the sensor and reference surface of approximately 0.5–1.0 millimeters (mm), an oscillation amplitude of approximately 0.1–0.3 mm, and an oscillation frequency of about 500–1,000 Hertz produced an acceptable signal. However, it is desirable to minimize the average plate separation to maximize the capacitor signal, and it is also desirable to minimize the coil-to-reference element distance to reduce the power required to actuate the reference surface oscillation as well as to reduce the strength of any stray electromagnetic fields contributing to the background noise. A small average plate separation maximizes the capacitor signal because the amplitude of the reference plate motion, although small on an absolute scale, is large relative to the plate separation, thereby producing a large change in capacitance. A small average plate separation also allows higher oscillation frequencies to be used because of the small absolute amplitude necessary. Edge card connector 86 provides connections for power to resistance heater 44 and for the signal output from sensor element 40 to circuit 20. Shield 88 shields circuit 20 from interference.

FIG. 5(b) is a cross sectional view of an illustrative embodiment of the present invention through a plane orthogonal to the plane of the view in FIG. 5(a). Apertures 76 and 78 define a gas flow path through the structure permitting the gas to come into contact with the sensor element. The gas flow path may be connected to a pump or other means for forcing gas to flow past the sensor surface, or the apertures may be left disconnected, to allow natural circulation to bring the mixture into contact with the sensor surface.

Figure 6:
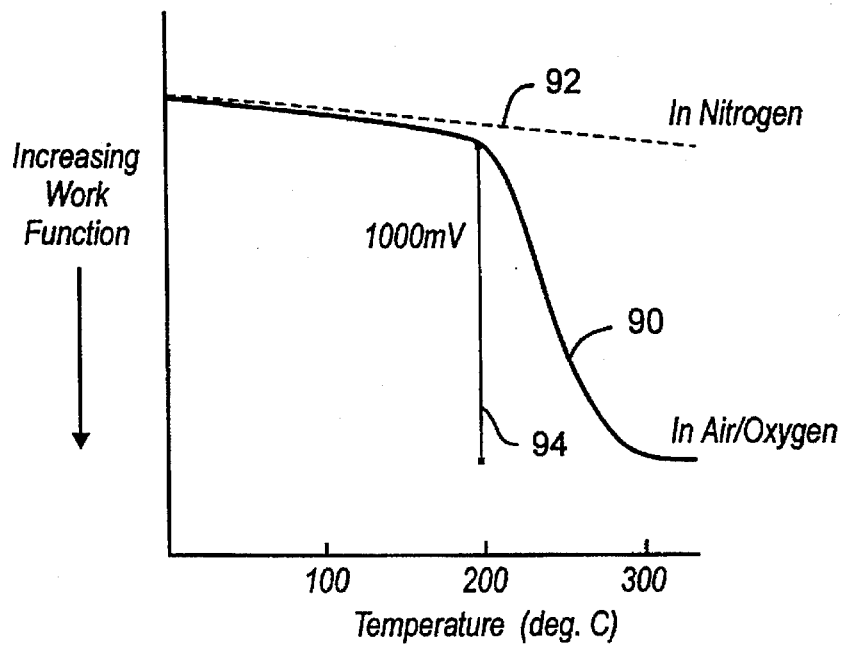
FIG. 6 is a response curve showing the work-function changes of a gold-film sensor as a function of temperature in air, oxygen, and nitrogen.

Experimental data taken using alternate embodiments of the invention are summarized in FIGS. 6–11. FIG. 6 is a curve showing the work-function changes of an embodiment of the present invention using a gold-film sensor on alumina as a function of temperature in air or oxygen, as shown by line 90, and in nitrogen, as shown by line 92. When the sensor surface was heated in air from ambient temperature to approximately 200° C., its work function increased linearly by an amount on the order of microvolts per degree Celsius (μv/°C.). However, when the sensor reached approximately 200° C., the change in work function began to increase rapidly until reaching a temperature of about 320° C. Between these two temperatures a dramatic increase of over 1000 millivolts (mV) was obtained, as shown by the vertical scale line 94. An identical response was observed when the sensor was heated in pure oxygen, but not in nitrogen. In both air and pure oxygen, this increase is completely reversible and nonlinear. When, however, the experiment was performed in a nitrogen atmosphere, as shown by line 92, little change in the work function was observed when the sensor was heated from ambient to 350° C. However, when the sensor was maintained at 320° C. and oxygen introduced into the nitrogen atmosphere, the work function increased rapidly to approximately 1000 mV. Repeated exposure to nitrogen followed by air demonstrated that the response was reversible. Similar behavior has been observed for an alternate embodiment of the present invention utilizing a platinum-film sensor element, except that the onset of the increase in work function upon exposure to oxygen occurred at a lower temperature of approximately 150° C.

The increase in work function is strongly dependent upon the nature of the substrate. For example, a 6,000Å gold film on alumina sensor exhibited a 1,000 mV increase in work function on heating, whereas similar gold films on a very flat polyimide substrate showed only a 300 mV increase on heating. Since the gold surface is much smoother on the polyimide surface than on the highly granular alumina surface, the difference in response is believed to result from the different gold-film morphologies and defect structures produced by these substrates. It appears that the high grain boundary densities in granular metal films result in the largest response to oxygen as well as the highest sensitivity to combustible gases.

Figure 7:
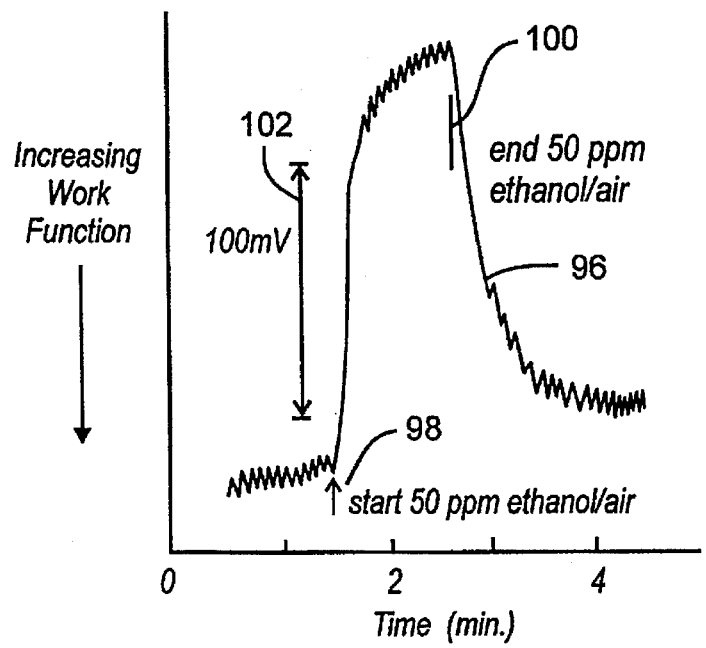
FIG. 7 is a response curve showing work-function changes of a gold-film sensor heated to 250° C. as a function of time upon exposure to 50 parts per million of ethanol in air for 1 minute.

FIG. 7 is a curve 96 showing work-function changes of the preferred embodiment of the present invention where the gold-film sensor is heated to 250° C. as a function of time upon exposure to 50 parts per million ("ppm") of ethanol in air for one minute. Upon exposure of the sensor to ethanol, indicated by arrow 98, a stable steady-state signal of approximately 150 mV is developed within one minute, as may be seen by reference to arrow 100 and vertical scale line 102. Upon exposure to pure air, initiated at arrow 100, the sensor returns to the baseline also within about one minute. Since the response at the sensor surface is essentially instantaneous, the speed of response reflected in this experiment is that of the flow dynamics, not the sensor itself. The sensor response to ethanol occurs in the same temperature range as the oxygen-activation process, so that below about 200° C., which is the threshold temperature for oxygen activation of a gold surface, there was essentially no signal.

Figure 8:
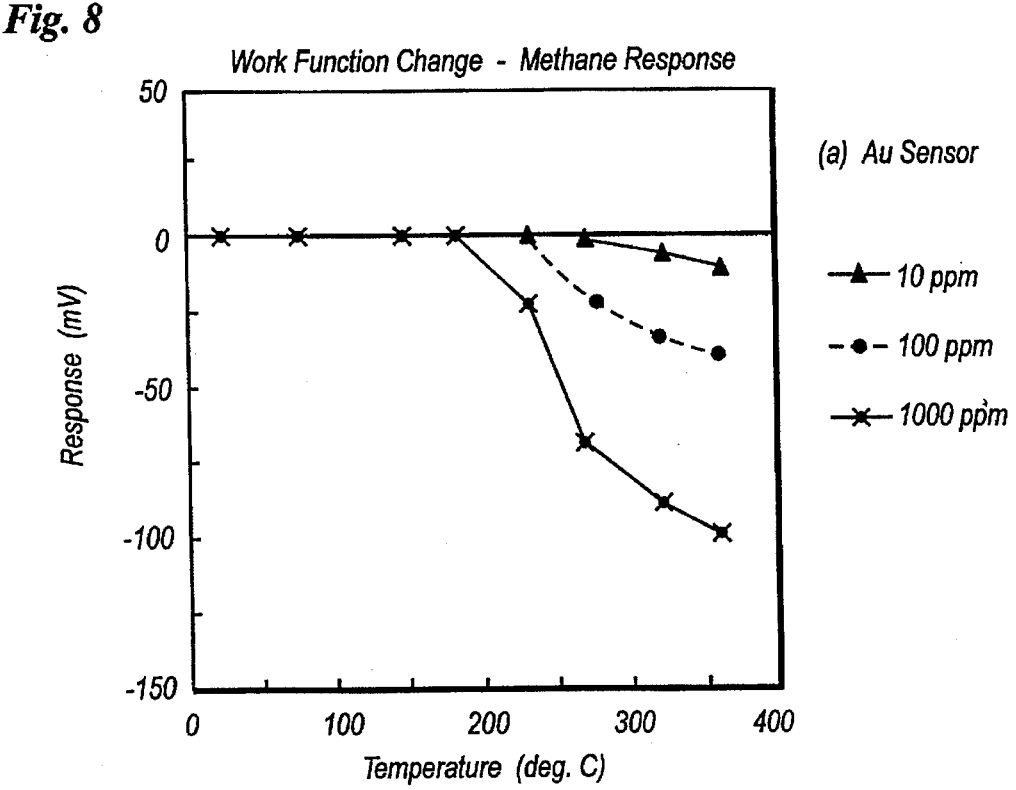
FIG. 8 is a response curve showing the work-function changes of a gold-film sensor as a function of temperature upon exposure to 10, 100, and 1,000 parts per million of methane.

FIG. 8 is a group of curves showing work-function changes of a gold-film sensor embodiment of the present invention as a function of temperature upon exposure to 10 ppm of methane represented by the curve having (▲) symbols, 100 ppm of methane represented by the curve having (●) symbols and 1,000 ppm of methane represented by the curve having (■) symbols. The response increases rapidly above about 200° C., which is consistent with the oxygen-activation process, whereby reactive oxygen adsorbed to the gold surface above 200° C. is then removed by reaction with methane. In contrast, no response was observed when an embodiment of the present invention incorporating a platinum-film sensor was used, which indicates that the activity of oxygen above the oxygen-activation threshold temperature for platinum (150° C.) is not sufficient to react with methane, demonstrating that different metal surfaces are capable of becoming oxygen activated to different degrees.

Figure 9:
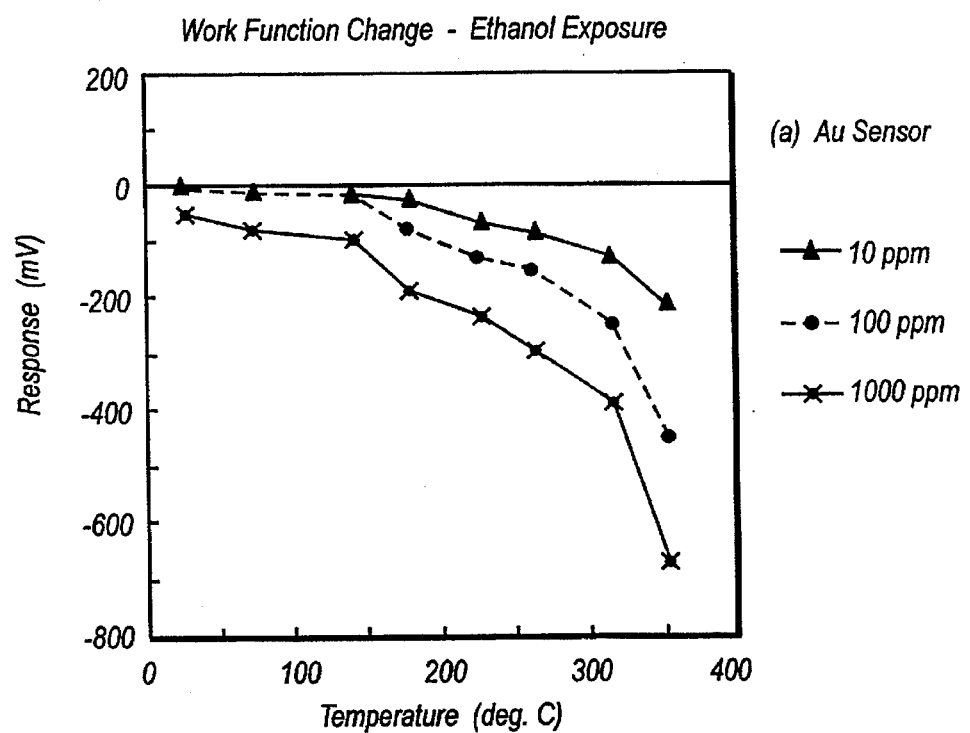
FIG. 9 is a response curve showing the work-function changes of a gold-film sensor as a function of temperature upon exposure to 10, 100, and 1,000 parts per million of ethanol.

FIG. 9 is a group of curves showing work-function changes of a gold-film sensor embodiment of the present invention as a function of temperature upon exposure to 10 ppm of ethanol represented by the curve having (▲) symbols, 100 ppm of ethanol represented by the curve having (●) symbols, and 1,000 ppm of ethanol represented by the curve having (■) symbols. The response at temperatures below the oxygen-activation threshold temperature of gold (200° C.) is believed to be due to adsorption of ethanol on the gold surface, since no response is observed when the ethanol is removed. At intermediate temperatures (200° C. to 300° C.) there are believed to be two competing reactions: ethanol adsorption/desorption and active oxygen that is removed by ethanol oxidation. At higher temperatures (greater than about 300° C.), it is believed that ethanol adsorption is absent, primarily because the gold surface is covered with active oxygen, so that the sole effect that causes the response is the decrease in active oxygen concentration. The same general considerations also apply to the response of an embodiment of the present invention incorporating a thin-film platinum sensor. Similar qualitative behavior also has been observed for the organic alcohol methanol, the ether ethyl ether, the ketone acetone and the alkene ethylene, except that the quantitative response curves are different for each gas and sensor metal combination. Therefore, by operating the sensor at a sufficiently high temperature above the oxygen-activation threshold temperature, active oxygen removal becomes the dominant reaction mechanism for organic combustible gases.

Figure 10:
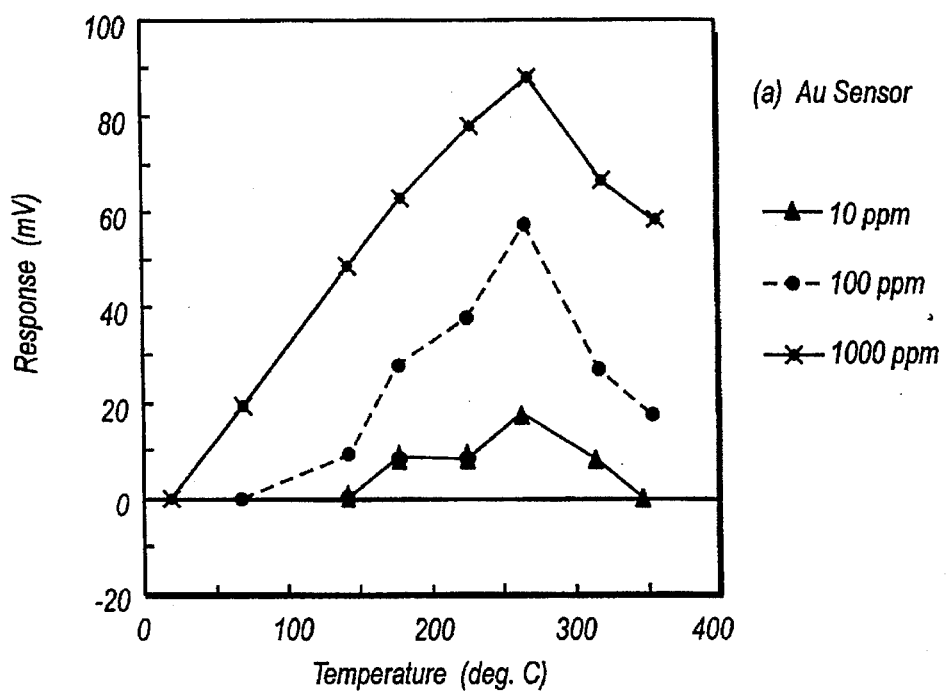
FIG. 10 is a response curve showing the work-function changes of a gold-film sensor as a function of temperature upon exposure to 10, 100, and 1,000 parts per million of carbon monoxide.

FIG. 10 is a group of curves showing work-function changes of the gold film sensor embodiment of the present invention as a function of temperature upon exposure to 10 ppm of carbon monoxide represented by the curve having (▲) symbols, 100 ppm of carbon monoxide represented by the curve having (●) symbols, and 1,000 ppm of carbon monoxide represented by the curve having (■) symbols. The same considerations as discussed with reference to FIG. 9 also apply here, except that the adsorption of carbon monoxide at lower and intermediate temperatures causes a complete change in the sign of the response prior to the creation of a pronounced response maximum at higher temperatures (greater than about 300° C.). Similar qualitative behavior has been observed for an alternate embodiment of the present invention incorporating a thin-platinum-film sensor and also for exposure of both embodiments to hydrogen and ammonia, except that the quantitative response curves are different for each gas and sensor combination. These results suggest that the multicomponent analysis of several gases in a stream is feasible using a relatively simple sensor array consisting of two or more different sensors based upon the operating temperature of the individual sensors and their composition. Unlike other sensing methods, the sign as well as the magnitude of the signal at different temperatures can be used to speciate a mixture of gases.

Figure 11:
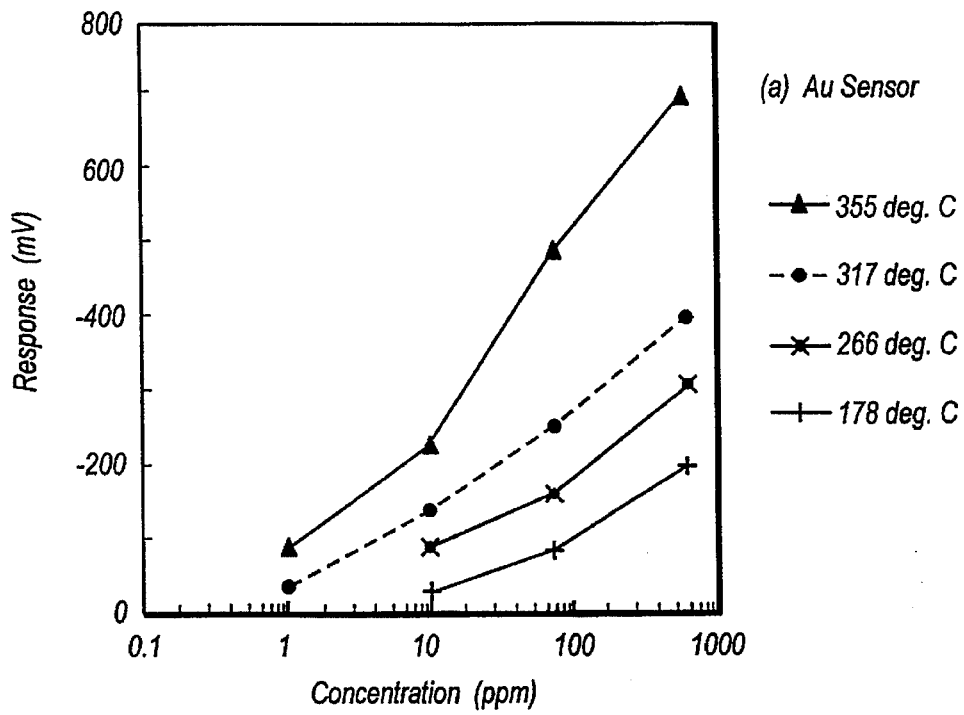
FIG. 11 shows the work-function response of a gold-film sensor to ethanol as a function of ethanol concentration at 178° C., 266° C., 317° C., and 355° C.

FIG. 11 is a group of curves showing the response of the preferred embodiment of the present invention to ethanol as a function of ethanol concentration at various temperatures. The curve having (+) symbols represents the response of a sensor maintained at 178° C.; the curve having (■) symbols, 266° C.; the curve having (●) symbols, 317° C.; and the curve having (▲) symbols, 355° C. The response varies approximately linearly with the logarithm of the concentration. This log-linear relationship is consistent with a steady-state balance between adsorption and desorption of molecules on the sensor surface and reduced response as surface sites for adsorption approach saturation at higher concentrations. The lower limit of detection is approximately 100 parts per billion, which is typical of most of the gases studied and is well below the detection level of existing solid-state combustible-gas sensors which generally are limited to detection ranges on the order of 50 ppm or more.

Based on an analysis of the response results, preferred operating temperatures that maximize the overall magnitude and speed of response have been established for both gold and platinum thin-film sensors on alumina substrates and are shown in Table 1.

TABLE 1

Preferred temperatures for combustible gas detection using alumina substrates.

| Gas | Temperature °C. | |
|---|---|---|
| | Platinum Film | Gold Film |
| Ethanol | >350 | >350 |
| Acetone | >350 | >350 |
| Ether | >350 | >350 |
| Methanol | >350 | >350 |
| Ethylene | >350 | >350 |
| Methane | a | >350 |
| Carbon Monoxide | 200 | 275 |
| Hydrogen | 200 | 225 |
| Ammonia | 130 | 80 |

[a]Methane could not be detected in these experiments even at the highest sensitivities.

Although the foregoing data were collected using pure gold and pure platinum sensor surfaces, it follows from the above results that alloys of gold and platinum should also exhibit oxygen activation and, hence, be useful as materials for sensor elements for combustible gas detection. Other noble metals that are expected to demonstrate oxygen activation are silver, palladium, rhodium and iridium. Based on average oxygen desorption temperatures measured in ultra high vacuum experiments, the oxygen activation temperatures are expected to follow the order Ag<Au<Pt<Pd<Ir<Rh. Therefore, it is reasonable to expect that oxygen-activated thin-film sensors fabricated from these noble metals and/or alloys can function over a wide range of operating temperatures and combustible-gas concentrations to permit a wide range of applications.

Although the foregoing discussion has focused primarily on use of the present invention as a combustible gas sensor, it should also be noted that, because oxygen activation depends on oxygen being present in the gas stream, the present invention is equally capable of functioning as an oxygen sensor, as demonstrated by the reversibility of the reaction discussed with reference to FIG. 6. The present invention also may, under certain circumstances, function as an oxygen/fuel ratio sensor as well. However, because the present invention is capable of operating in gas streams at temperatures well below those at which $Y_2O_3$-doped solid-electrolyte-based solid-state devices operate, without being subject to false readings caused by moisture or other common interference gases, the present invention, if used for example as an air/fuel ratio sensor in an automobile engine control system, would provide nearly instantaneous feedback, thereby reducing or eliminating the period during which the engine must operate in an open-loop condition after a cold start.

The present invention overcomes the limitations in the prior art for combustible-gas detection by operating the noble metal sensor surface at an elevated temperature, which is required for oxygen activation, as well as by employing durable noble-metal sensor place surfaces, such as gold. By operating the sensor at elevated temperature: (1) the sensor can operate continuously and in real time without the sensor surface becoming saturated because the sensor surface is being regenerated continuously by oxygen in the gaseous mixture; (2) impurities desorb from the sensor surface at elevated temperatures, so that contamination effects are minimized; and (3) the sensor operation is unaffected by completely oxidized molecules in the gaseous mixture, such as carbon dioxide and water vapor, since no further oxidation of these molecules is possible. Furthermore, in the preferred embodiment, where work function, rather than some other property, is measured, the thicknesses of the sensor and reference films are immaterial, since only their surfaces contribute to the work-function response.

These innovations have achieved the desired reversible reactions at the sensor surfaces that have permitted circuit 20 to be used to evaluate the work-function change for several noble-metal sensor elements and combustible gases with a typical precision of ±3 mV. Although the preferred embodiment presently exploits change in work function to measure the instantaneous status of gas adsorption, other properties affected by gas adsorption, such as resistance, may also be exploited. Initial experiments have indicated that sufficiently thin films (less than about 1,000Å) are required for the detection of combustible gases by resistance methods. For example, at 250° C., an 800Å platinum film exhibited an increase in resistance from 6 MegaOhms (MΩ) to 10 MΩ in air and a further increase in resistance to 11 MΩ upon exposure to methanol at concentrations of several hundred parts per million.

Although certain preferred embodiments of the invention and methods of fabrication and implementation thereof have been described herein, it will be apparent to those skilled in the art from the foregoing description that variations and modifications of the disclosed embodiments and methods may be made without departing from the true spirit and scope of the invention. Accordingly, it is intended that the invention shah be limited only to the extent required by the appended claims and the rules and principles of applicable law.

What is claimed is:

1. An apparatus for sensing at least one combustible gas in a gaseous mixture also containing oxygen, said apparatus comprising:

a sensor element having an exposed surface, said sensor element being composed of metal chosen from the group consisting of noble metals and noble metal alloys;

means for heating at least the exposed surface of the sensor element to a temperature above the oxygen activation temperature and below the oxygen desorption temperature of the noble metals or noble metal alloys of the sensor element;

structure supporting the sensor element for exposure to said gaseous mixture to cause a dynamic adsorption and desorption of oxygen and an oxidized product of said at least one combustible gas, where present, onto said exposed surface; and a circuit to detect a change in a predetermined electrical property of the sensor element resulting from adsorption and desorption of said at least one combustible gas, whereby the presence of said at least one combustible gas is indicated by the change in said electrical property.

2. The apparatus of claim 1 wherein:

the circuit to detect change in a predetermined property of the sensor element comprises a circuit adapted to detect change in work function of said sensor element.

3. The apparatus of claim 1 further including:

a reference element composed of an electrically conducting material having a surface that is incapable of becoming oxygen activated;

structure supporting said reference element in a spaced-apart confronting relationship to the exposed surface of the sensor element to form a capacitor; and means for varying capacitance of said capacitor to cause a fluctuating current in a circuit containing said capacitor;

wherein the circuit to detect change in a predetermined property of the sensor element comprises a circuit to detect modulation of the fluctuating current resulting from change in work function of the sensor element.

4. The apparatus of claim 3 wherein the reference element is composed of chromium-contaminated gold.

5. The apparatus of claim 1 further including:

means for measuring instantaneous temperature of the sensor element, whereby the change in predetermined electrical property is determined as a function of temperature.

6. The apparatus of claim 1 wherein the sensor element is composed of a material chosen from the group consisting of gold, platinum, and alloys of gold and platinum.

7. The apparatus of claim 1 wherein:

the sensor element comprises a film having a thickness of less than 1,000Å and having two leads connected thereto; and the circuit to detect change in an electrical property of the sensor element comprises a circuit containing the sensor element adapted to detect change in resistance of said sensor element.

8. The apparatus of claim 7 further including:

a reference element, electrically matched to the sensor element, composed of an electrically conducting material having a surface that is incapable of becoming oxygen activated;

structure supporting said reference element for exposure to said gaseous mixture.

9. An apparatus for sensing a constituent gas in a gaseous mixture, said apparatus comprising:

a sensor element having an exposed surface, said sensor element being composed of metal chosen from the group consisting of noble metals and noble metal alloys;

a first substrate to which the sensor element is affixed;

means for heating at least the exposed surface of the sensor element to a temperature above the oxygen activation temperature and below the oxygen desorption temperature of the noble metals or noble metal alloys of the sensor element;

a reference element composed of an electrically conducting material having a surface that is incapable of becoming oxygen activated;

a second substrate to which the reference element is affixed;

a circuit adapted to detect change in a fluctuating current, said circuit including a capacitor, the sensor element and the reference element comprising the plates of said capacitor;

structure supporting the sensor element and the reference element with their surfaces in a confronting, spaced-apart configuration to form the capacitor;

means for varying capacitance of the capacitor to cause a fluctuating current in said circuit; and means for exposing the sensor element to the gaseous mixture to cause a dynamic adsorption and desorption of said constituent gas onto said exposed surface;

whereby the presence of said constituent gas is indicated by detecting change in the fluctuating current caused by change in work function of the sensor element resulting from adsorption and desorption of said constituent gas on said sensor element.

10. The apparatus of claim 9 wherein the reference element is composed of chromium-contaminated gold.

11. The apparatus of claim 9 further including:

means to monitor instantaneous temperature of the sensor element, whereby the change in predetermined electrical property is determined as a function of temperature.

12. The apparatus of claim 9 wherein the constituent gas to be detected is oxygen.

13. The apparatus of claim 9 wherein the constituent gas to be detected is at least one combustible gas and the gaseous mixture also contains oxygen.

14. The apparatus of claim 9 in which:

the sensor element comprises a film having a thickness of less than 6,000 Angstroms;

the first substrate comprises a plate of alumina;

the second substrate comprises a plate of magnetizable metal having a proximal end and a distal end;

the reference element is affixed to the second substrate at the distal end thereof;

the structure supporting the sensor element comprises a frame fixing the sensor element and the reference element in a parallel, confronting configuration to form a parallel-plate capacitor;

the frame attaches to the magnetizable metal substrate at the proximal end, said substrate thereby forming a cantilever; and the means for varying capacitance comprises a fluctuating magnetic field acting on the magnetizable metal substrate of the reference element to cause said magnetizable metal substrate to fluctuate mechanically.

\* \* \* \* \*